United States Patent [19]

Bitter

[11] Patent Number: 5,310,660
[45] Date of Patent: May 10, 1994

US005310660A

[54] METHOD AND A HYBRID PROMOTER FOR CONTROLLING EXOGENOUS GENE TRANSCRIPTION

[75] Inventor: Grant A. Bitter, Thousand Oaks, Calif.

[73] Assignee: Amgen, Thousand Oaks, Calif.

[21] Appl. No.: 769,472

[22] Filed: Oct. 1, 1991

Related U.S. Application Data

[63] Continuation of Ser. No. 336,604, Apr. 7, 1989, abandoned, which is a continuation of Ser. No. 720,587, Apr. 8, 1985, abandoned.

[51] Int. Cl.$^5$ ............. C12N 15/00; C12N 15/63; C12N 15/81; C12P 21/00
[52] U.S. Cl. ............. 435/69.1; 435/172.3; 536/24.1; 935/28; 935/37
[58] Field of Search ............. 435/91, 172.1, 172.3, 435/255, 256, 320.1, 69.1, 69.9; 536/27, 23, 52, 23.72, 24.1; 935/28, 37.69

[56] References Cited

U.S. PATENT DOCUMENTS 5,089,398 2/1992 Rosenberg et al. ............. 435/69.1

FOREIGN PATENT DOCUMENTS

| 0072318 | 2/1983 | European Pat. Off. | 435/172.3 |
| 0073657 | 3/1983 | European Pat. Off. | 435/172.3 |
| 0077670 | 4/1983 | European Pat. Off. | |
| 0128743 | 12/1984 | European Pat. Off. | 435/172.3 |
| 2137208 | 3/1984 | United Kingdom | 435/172.3 |

OTHER PUBLICATIONS

Gray et al, Nature 295: 511 (1982).
Beggs, *Nature*, 275, 104–109 (1979).
Bennetzen, et al., *J. Biol. Chem.*, 257, 3018–3025 (1982).
Bitter, et al., *Gene*, 32, 263–274 (1984).
Caruthers, Chemical & Enzymatic Synthesis of Gene Fragments, 71–79 (1982).
Citron, et al., *J. Bacteriol.*, 158, 269–278 (1984).
Derynck, et al., *Nucleic Acids Res.*, 11, 1819–1837 (1983).
Fitzgerald-Hayes, et al. *Cell*, 29, 235–244 (1982).
Fried, et al. *Mol. Cell. Biol.*, 5, 99–108 (1985).
Guarente *Cell*, 36, 799–800 (1984).
Guarente, et al. *Cell*, 36, 503–511 (1984).
Guarente, et al. *Proc. Natl. Acad. Sci.*, 79, 7410–7414 (1982).
Hinnen, et al. *Proc. Natl. Acad. Sci.*, 74, 1929–1933 (1978).
Hitzeman, et al. *Nucleic Acids Res.*, 10, 7791–7808 (1982).
Holland, et al. *Biochemistry*, 17, 4900–4907 (1978).
Holland, et al. *J. Biol. Chem.*, 258, 5291–5299 (1983).
Johnston, et al. *Mol. Cell. Biol.*, 4, 1440–1448 (1984).
Jones, et al. *FEBS Lett.*, 22, 185–189 (1972).
Kingsman, et al. *Gene*, 7, 141–153 (1979).
Krebs *J. Biol. Chem.*, 200, 471–478 (1953).
Maitra, et al. *J. Biol. Chem.*, 246, 475–488 (1971).
Matsumoto, et al. *J. Bacteriol.*, 153, 1405–1414 (1983).
Miozarri, et al. *J. Bacteriol.*, 134, 48–59 (1978).
Musti, et al. *Gene*, 25, 133–143 (1983).

(List continued on next page.)

*Primary Examiner*—James Martinell
*Attorney, Agent, or Firm*—Marshall, O'Toole, Gerstein, Murray & Borun

[57] ABSTRACT

A hybrid promoter for controlling exogenous gene transcription is constructed by insertion of a UAS$_G$ into a GPD portable promoter. The resulting hybrid promoter is placed upstream of an exogenous gene in a hybrid yeast-bacterial plasmid, which is used to transform yeast cells. Due to the regulation imparted to the GPD promoter by the UAS$_G$, transcription of the exogenous gene, and hence production of the exogenous gene product, may be regulated by controlling the composition of the carbon source in the yeast culture medium. Specifically, glucose is used to repress transcription and galactose is used to induce transcription.

18 Claims, 9 Drawing Sheets

OTHER PUBLICATIONS

Oshima "Regulatory Circuits for Gene Expression: The Metabolism of Galactose & Phosphate", in *The Molecular Biology of the Yeast, Saccharomyces: Metabolism & Gene Expression,* 159–180 (1982), Strathern, et al., eds.
Sanger, et al. *Proc. Natl. Acad. Sci.,* 74, 5463–5467 (1977).
Stinchcomb, et al. *Nature,* 282, 39–43 (1979).
Stinchcomb, et al. *Proc. Natl. Acad. Sci.,* 77, 4559–4563 (1980).
Struhl, et al. *Proc. Natl. Acad. Sci.,* 76, 1035–1039 (1979).
Thomas *Proc. Natl. Acad. Sci.,* 77, 5201–5205 (1980).
Tschumper, et al. *Gene,* 23, 221–232 (1983).
Tschumper, et al. *Gene,* 10, 157–166 (1980).
Valenzuela, et al. Animal Virus Genetics, B. Fields et al., eds., Academic Press, 57–70.
Weck, et al. *J. General Virology,* 57, 233–237 (1982).
West, et al. *Mol. Cell. Biol.* 4, 2467–2478 (1984).
Yocum, et al. *Mol. Cell. Biol.,* 4, 1985–1998 (1984).
Zaret, et al. *Cell,* 28, 563–573 (1982).
Beier et al., Nature, 300, 724–728 (1982).
Struhl, Proc. Nat'l Acad. (USA), 81, 7865–7869 (1984).

METHOD AND A HYBRID PROMOTER FOR CONTROLLING EXOGENOUS GENE TRANSCRIPTION

This application is a continuation of application Ser. No. 07/336,604, filed Apr. 7, 1989, now abandoned, which is a continuation of Ser. No. 720,587, filed Apr. 8, 1985, now abandoned.

BACKGROUND

The present invention pertains in general to methods and hybrid promoters for controlling transcription of exogenous genes and in particular to methods and hybrid promoters for controlling transcription of exogenous genes in yeast.

A number of microorganisms, including bacteria and yeasts, are useful for the manufacture of substantial quantities of biological products the synthesis of which is directed by genes which are foreign to the microorganisms employed ("exogenous genes"). In particular, there is considerable interest in the production of exogenous gene products in yeast cells because yeast cells are able to attach carbohydrates (i.e., to glycosylate) proteins for the expression of active glycoprotein gene products; they are able to process protein gene products in a way which permits secretion of the gene products; and they are able to present surface antigens, e.g., hepatitis B surface antigens (HBsAg), in a way which enhances their immunogenicity. Moreover, yeasts appear on the list of organisms generally regarded as safe (GRAS) and extensive commercial fermen technology has been developed for their fermentation in the baking and brewing industries.

In general, genes encoding protein products are segments of double-stranded deoxyribonucleic acid (DNA), one strand of which is transcribed into a single strand of messenger ribonucleic acid (mRNA) through the action of RNA polymerase II. The mRNA is translated into proteins which may be further processed for secretion and glycosylation. In order for the gene to be transcribed, an initiation complex must be formed between RNA polymerase and DNA in the region near the first nucleotide base to be transcribed, i.e., at the "upstream" end of the gene. The mRNA is then synthesized as the RNA polymerase moves downstream along the gene until it reaches a DNA site, called a terminator, at which transcription ceases. The entire 5'-flanking sequence of DNA which is upstream from the gene and which is competent to promote transcription initiation complex is known as a promoter. Within the promoter and near (generally 25 to 150 base pairs upstream of) the point at which the first nucleotide is incorporated into mRNA (the start point of the transcription initiation complex), the sequence of seven base pairs known as the TATA box homology is found. The TATA box homology is apparently required for fixing transcription initiation at a specific distance downstream. The TATA box homology has the consensus sequence although minor variations of this sequence have been observed.

In yeast, certain sites called upstream regulatory sequences or upstream activation sequences (UASs) have been located at sites hundreds of nucleotides upstream of the region of transcription initiation. These UASs regulate transcription in response to particular physiological signals. Guarente, *Cell,* 36: 799–800 (1984).

One UAS, called $UAS_G$ for upstream activating sequence-galactose, is found between genes coding for two enzymes involved in the metabolism of galactose, the GAL 1 gene coding for galactokinase and the GAL 10 gene coding for UDP-galactose epimerase. The major transcription initiation sites of the GAL 1 and GAL 10 genes are separated by 606 base pairs of DNA on yeast chromosome II. Johnston, et al., *Mol.Cell.Biol.,* 4: 1440–1448 (1984).

The GAL 1 and GAL 10 genes are transcribed in opposite directions (divergently transcribed) from an intergenic region. The start point for the GAL 1 gene is downstream of a TATA box on a strand opposite the strand on which the start point for the GAL 10 gene is located downstream of a second TATA box. DNA sequences within this GAL 1/GAL 10 intergenic region mediates the regulation of both genes by carbon source. Yocum, et al., *Mol.Cell.Biol.,* 4: 1985–1998 (1984).

These genes are expressed at a low, basal level when the yeast cells containing them are grown in non-fermentable carbon sources, such as lactate, glycerol or ethanol. Transcription of the genes is induced 1,000-fold by growth in galactose On the other hand, these genes are subject to catabolite repression in that cells growing in glucose are not fully inducible by galactose.

The $UAS_G$ is controlled by other genes which activate or repress transcription. A GAL 80 gene encodes a negative regulator which is hypothesized to function by binding to and inactivating a protein produced by a GAL 4 gene. In the presence of galactose, the GAL 80 regulator is non-functional and the GAL 4 protein activates transcription. Oshima, "Regulatory Circuits for Gene Expression: The Metabolism of Galactose and Phosphate", in *The Molecular Biology of the Yeast Saccharomyces: Metabolism and Gene Expression,* Strathern, et al., eds., Cold Spring Harbor Laboratory, N.Y., 159–180 (1982). Several genes, including a GAL 82 gene and a GAL 83 gene, are involved in glucose repression, but their mode of action has not been well defined. Matsumoto, et al., *J.Bacteriol.,* 153: 1405–1414 (1983).

The properties of UASs may be examined by the endonuclease-mediated substitution of a UAS from a first promoter for a different UAS of a second promoter or by endonuclease-mediated insertion of a UAS in a functional promoter (i.e., either substitution or insertion of an extrinsic UAS). Guarente, et al., *Proc.Natl.Acad.-Sci. (U.S.A.)* 7410–7414 (1982); Fried, et al., *Mol.Cell-.Biol.,* 5: 99–108 (1985). Substitutions of and insertions of $UAS_G$ include the substitution of $UAS_G$ for the UAS of an inducible gene (CYC 1) by Guarente, et al., supra, which is reported as indicating that the $UAS_G$ employed does not appear to contain sequences mediating glucose repression despite conferring galactose inducibility, and the insertion of the same $UAS_G$ in constitutive promoters (ribosomal proteins tcm 1 and cyh 2) by Fried, et al., supra, which is reported as conferring both galactose inducibility and glucose repressibility.

The activity of a promoter or of a UAS/promoter hybrid (a "hybrid promoter") is commonly monitored by assaying for the level of a specific protein which is the ultimate product of the gene regulated by the promoter. UASs may be placed at various distances from the site of transcription initiation or may be inverted [Fried, et al., supra; Guarente, et al., *Cell*, 36: 503–511 (1984)], and functional UASs may constitute sub-fragments of the initial DNA segment used [West, et al., *Mol.Cell.Biol.*, 4: 2467–2478 (1984)]. The combination of UAS/promoter/test gene is generally assembled within a yeast-bacterial shuttle vector.

Plasmids are circular, double-stranded DNA structures which replicate independently of chromosomal DNA. Yeast-bacterial shuttle vectors contain a sequence of DNA, including a DNA replication initiation site such as the so-called 2μ origin of replication, recognized by the replication enzymes and factors of yeast cells. Yeast-bacterial shuttle vectors also contain an origin of replication from a bacterial plasmid including an initiation site recognized by the replication enzymes and factors of bacterial cells. Beggs, *Nature*, 275: 104–109 (1979); Stinchcomb, et al., *Proc.Natl.Acad.Sci. (U.S.A.)*, 77: 4559–4563 (1980). These shuttle vectors are able to replicate in and may be selected in and recovered from both the bacterium *Escherichia coli* (*E.-coli*), where it is convenient to construct and multiply (amplify) the plasmids, and the yeast *Saccharomyces cerevisiae* (*S.cerevisiae*), in which the plasmid may be used as a transformation vector to obtain expression of foreign DNA. Stinchcomb, et al., *Nature*, 282: 39–43 (1979); Kingsman, et al., *Gene*, 7: 141–153 (1979); and Tschumper, et. al., *Gene*, 10: 157–166 (1980).

Bacterial-yeast shuttle vectors may be practically employed in the transformation of yeast cells. One such vector, designated YRp7, contains a chromosomal ARS sequence which allows autonomous replication, as well as the TRP1 gene, which codes for an enzyme essential for the production of tryptophan called N-(5′-phosphoribosyl) anthranilate isomerase. Therefore, the TRP1 gene may be used as a marker to select for the presence of YRp7 within a yeast cell, such as one having the genotype trp1, which is otherwise incapable of manufacturing the essential amino acid tryptophan. Struhl, et al., *Proc.Natl.Acad.Sci. (U.S.A.)*, 76: 1035–1039 (1979).

Studies of the gene CYC 1, the product of which is iso-1-cytochrome c, demonstrate the importance of proper termination of transcription. Improper transcription termination results in continuation of transcription into a neighboring gene. Zaret, et al., *Cell*, 28: 563–573 (1982). Efficient transcription of yeast DNA into mRNA appears to be dependent upon the presence of a site for addition of a tail containing adenine-containing nucleotides, called a poly-A tail, or a transcription termination sequence or both at or near the downstream (3′) end of a polypeptide coding region of a gene.

Such bacterial-yeast hybrid vectors, often referred to as shuttle vectors, may be used to obtain expression of genes from other organisms (exogenous genes) in yeast cells. Heptatitis B surface antigen (HBsAg) has been produced by means of a 3-phosphoglycerate kinase (PGK) promoter (Hitzeman, et al., European Patent Application No. 73657), the arg 3 promoter (Cabezon, et al., European Patent Application No. 106828), a promoter from an alcohol dehydrogenase (ADH 1) gene (Rutter, et al., European Patent Application No. 72318), and a glyceraldehyde-3-phosphate dehydrogenase (GPD) promoter [Bitter, et al., *Gene*, 32: 263–274 (1984)]. A different GPD promoter has been used to obtain expression of thaumatin-like proteins and chymosin-like proteins. Edens, et al., European Patent Application No. 129268. Bovine calf prochymosin, bovine growth hormone, human leukocyte interferon, renin and prorenin may be expressed in yeast by fusion with a GAL 1 promoter. Strausberg, et al., European Patent Application No. 128743; Botstein, et al., U.K. Pataent Application No. 2137208A.

Yeast genes encoding glycolytic enzymes are expressed at high levels. Yeast expression vectors employing glycolytic enzyme promoters such as the ADH promoter [Hitzeman, et al., *Nucleic Acids Res.*, 10: 7791–7808 (1982)] and the promoter for the phosphoglycerate kinase (PGK) gene [Derynck, et al., *Nucleic Acids Res.*, 11: 1819–1837 (1983)] may be constructed.

In particular, the glycolytic enzyme GPD is a promising promoter for use in the expression of exogenous genes. GPD accounts for up to 5% of the dry weight of commercial baker's yeast [Krebs, *J.Biol.Chem.*, 200: 471–478 (1953)] and the mRNA which encodes this enzyme represents 2–5% of the total yeast poly-A-containing mRNA [Holland, et al., *Biochemistry*, 17: 4900–4907 (1978)]. *S. cerevisiae* contains three non-tandemly repeated structural genes for GPD, all of which are transcribed in vegetatively growing yeast. Holland, et al., *J.Biol.Chem.*, 258: 5291–5299 (1983); Musti, et al., *Gene*, 25: 133–143 (1983). The product of one of the three GPD genes, that encoded by the gene on PGAP 491, accounts for most of the cellular GPD enzyme. Jones, et al., *FEBS Lett.*, 22:185–189 (1972); Holland, et al., *J.Biol.Chem.*, 258: 5291–5299 (1983). Thus, the GPD promoter of this gene is expected to be highly useful in the production of large quantities of exogenous gene products.

Despite the advantages of yeast as a host for exogenous genes, some exogenous gene products, such as human immune interferon (IFN-γ), are toxic to yeast. As a result, plasmids constitutively expressing IFN-γ are unstable and it is difficult to obtain high density cultures of yeast cells producing IFN-γ. Therefore, it is desirable to have some means for turning off (repressing) production of exogenous gene products until a high-density culture is obtained, as well as a means for turning on (inducing) production of exogenous gene products during a harvesting period.

SUMMARY OF THE INVENTION

A hybrid promoter according to the present invention effectively controls transcription of an exogenous gene in yeast. The hybrid promoter comprises an effective portion of a glyceraldehyde-3-phosphate dehydrogenase promoter into which an effective portion of an extrinsic upstream regulatory sequence has been inserted at a location upstream of a TATA box homology that is adjacent a downstream end of the hybrid promoter. The hybrid promoter is constructed so that the TATA box homology is positioned between the upstream regulatory sequence and the site of transcription initiation.

A hybrid promoter according to the present invention may comprise at least part of a glyceraldehyde-3-phosphate dehydrogenase promoter, including effective 5′ extensions, allelic variations and restriction site modifications thereof, and including a TATA box homology adjacent a downstream end of the promoter. At least part of an extrinsic upstream regulating sequence, essentially as given in Table I, infra, and including effective deletion fragments thereof, is inserted within the promoter at a location upstream from the TATA box homology.

A DNA segment mediating regulatable transcription in yeast according to the present invention comprises a hybrid promoter The hybrid promoter, in turn, comprises an effective portion of a glyceraldehyde-3-phosphate dehydrogenase promoter into which is inserted an effective portion of an extrinsic upstream regulatory sequence at a location in the glyceraldehyde-3-phosphate dehydrogenase promoter upstream of a TATA box homology that is adjacent a downstream end of the hybrid promoter. An exogenous gene is inserted downstream of the TATA box homology adjacent the downstream end of the hybrid promoter.

A method, according to the present invention, for controlling transcription of a gene in yeast involves inserting an effective portion of an exogenous upstream activating sequence upstream of a TATA box homology in a yeast glyceraldehyde-3-phosphate dehydrogenase promoter and introducing an exogenous gene downstream of the TATA box homology adjacent the downstream end of the hybrid promoter.

Another method according to the present invention controls exogenous gene product toxicity in yeast host cells while obtaining a high yield of the exogenous gene product. In this method, an exogenous gene is placed under the control of normally (i.e., in the absence of an inserted UAS) constitutive yeast promoter, such as a GPD promoter. The normally constitutive promoter is repressed during a phase of host cell proliferation by means of an extrinsic upstream regulatory sequence inserted with the constitutive promoter. When sufficient transformed host cells are present for efficient production of the exogenous gene product, inducing the normally constitutive promoter by means of the extrinsic regulatory sequence during an exogenous gene product production phase.

BRIEF DESCRIPTION OF THE DRAWINGS

FIG. 11 is an upstream regulatory sequence, UAS$^G$.

DETAILED DESCRIPTION

According to the present invention, a UAS is inserted at a restriction site in the GPD portable promoter, described in Bitter, et al., *Gene*, 32: 263-274 (1984). A plasmid, designated pΔ22(GPD), containing the GPD portable promoter was deposited with the American Type Culture Collection, Rockville, Md, on Sep. 5, 1991 and assigned A.T.C.C. Accession No. 75093.

The UAS is inserted upstream of the TATA box homology of the portable promoter. Insertion of a UAS confers regulation upon a promoter which is otherwise always turned on, i.e., a constitutive promoter.

Specifically, the *S. cerevesiae* GPD portable promoter has been modified at an AvaII site by introduction of an upstream regulatory sequence UAS$_G$, which has been published in Johnston, et al., *Mol.Cell.Biol.*, 4: 1440-1448 (1984) and which appears in Table I. The portion introduced in the examples of a hybrid promoter 1 and of the method according to the present invention is the portion between the DdeI and Sau3a restriction sites given in Table I. This portion will be hereinafter referred to as UAS$_G$.

TABLE I

| | 10 | | | 20 | | | 30 | | | 40 | |
|---|---|---|---|---|---|---|---|---|---|---|---|
| GAAT | TCG | ACA | GGT | TAT | CAG | CAA | CAA | CAC | AGT | CAT | ATC | CAT | TCT |
| CTTA | AGC | TGT | CCA | ATA | GTC | GTT | GTT | GTG | TCA | GTA | TAG | GTA | AGA |

| | 50 | | | 60 | | | 70 | | | 80 | |
|---|---|---|---|---|---|---|---|---|---|---|---|
| CAA | TTA | GCT | CTA | CCA | CAG | TGT | GTG | AAC | CAA | TGT | ATC | CAG | CAC |
| GTT | AAT | CGA | GAT | GGT | GTC | ACA | CAC | TTG | GTT | ACA | TAG | GTC | GTG |

| | 90 | | | 100 | | | 110 | | | 120 | |
|---|---|---|---|---|---|---|---|---|---|---|---|
| CAC | CTG | TAA | CCA | AAA | CAA | TTT | TAG | AAG | TAC | TTT | CAC | TTT | GTA |
| GTG | GAC | ATT | GGT | TTT | GTT | AAA | ATC | TTC | ATG | AAA | GTG | AAA | CAT |

| 130 | | | 140 | | | 150 | | | 160 | | |
|---|---|---|---|---|---|---|---|---|---|---|---|
| ACT | GAG | CTG | TCA | TTT | ATA | TTG | AAT | TTT | CAA | AAA | TTC | TTA | CTT |
| TGA | CTC | GAC | AGT | AAA | TAT | AAC | TTA | AAA | GTT | TTT | AAG | AAT | GAA |
| | | | GAL 10 | | | | | | | | |

| 170 | | | 180 | | | 190 | | | 200 | | | 210 |
|---|---|---|---|---|---|---|---|---|---|---|---|---|
| TTT | TTT | TGG | ATG | GAC | GCA | AAG | AAG | TTT | AAT | AAT | CAT | ATT | ACA |
| AAA | AAA | ACC | TAC | CTG | CGT | TTC | TTC | AAA | TTA | TTA | GTA | TAA | TGT |

| | 220 | | | 230 | | | 240 | | | 250 | |
|---|---|---|---|---|---|---|---|---|---|---|---|
| TGG | CAT | TAC | CAC | CAT | ATA | CAT | ATC | CAT | ATA | CAT | ATC | CAT | ATC |
| ACC | GTA | ATG | GTG | GTA | TAT | GTA | TAG | GTA | TAT | GTA | TAG | GTA | TAG |

TABLE I-continued

```
                260             270             280             290
                 .               .               .               .
     TAA TCT TAC TTA TAT GTT GTG AAA ATG TAA AGA GCC CCA TTA
     ATT AGA ATG AAT ATA CAA CAC CTT TAC ATT TCT CGG GGT AAT

Dde I⟶
          300             310             320             330
           .               .               .               .
     TC/T TA G CCT AAA AAA ACC TTC TCT TTG AAA CTT TCA GTA ATA
     AG A AT/C GGA TTT TTT TGG AAG AGA AAC TTT GAA AGT CAT TAT 340             350             360             370
                 .               .               .               .
     CGC TTA ACT GCT CAT TGC TAT ATT GAA GTA CGG ATT AGA AGC
     GCG AAT TGA CGA GTA ACG ATA TAA CTT CAT GCC TAA TCT TCG 380             390             400             410             420
      .               .               .               .               .
     CGC CGA GCG GGT GAC AGC CCT CCG AAG GAA GAC TCT CCT CCG
     GCG GCT CGC CCA CTG TCG GGA GGC TTC CTT CTG AGA GGA GGC 430             440             450             460
                 .               .               .               .
     TGC GTC CTC GTC TTC ACC GGT CGC GTT CCT GAA ACG CAG ATG
     ACG CAG GAG CAG AAG TGG CCA GCG CAA GGA CTT TGC GTC TAC 470             480             490             500
                 .               .               .               .
     TGC CTC GCG CCG CAC TGC TCC GAA CAA TAA AGA TTC TAC AAT
     ACG GAG CGC GGC GTG ACG AGG CTT GTT ATT TCT AAG ATG TTA 510             520             530             540
                 .               .               .               .
     ACT AGC TTT TAT GGT TAT GAA GAG GAA AAA TTG GCA GTA ACC
     TGA TCG AAA ATA CCA ATA CTT CTC CTT TTT AAC CGT CAT TGG 550             560             570             580
                 .               .               .               .
     TGG CCC CAC AAA CCT TCA AAT GAA CGA ATC AAA TTA ACA ACC
     ACC GGG GTG TTT GGA AGT TTA CTT GCT TAG TTT AAT TGT TGG 590             600             610             620             630
      .               .               .               .               .
     ATA GGA TGA TAA TGC GAT TAG TTT TTT AGC CTT ATT TCT GGG
     TAT CCT ACT ATT ACG CTA ATC AAA AAA TCG GAA TAA AGA CCC

⟵Sau 3A
                640             650             660             670
                 .               .               .               .
     GTA ATT AAT CAG CGA AGC GAT GAT TTT TG/A T CT ATT AAC AGA
     CAT TAA TTA GTC GCT TCG CTA CTA AAA AC T A/GA TAA TTG TCT 680             690             700             710
           .               .               .               .
     TAT ATA AAT GCA AAA ACT GCA TAA CCA CTT TAA CTA ATA CTT
     ATA TAT TTA CGT TTT TGA CGT ATT GGT GAA ATT GAT TAT GAA 720             730             740             750
                 .               .               .               .
     TCA ACA TTT TCG GTT TGT ATT ACT TCT TAT TCA AAT GTA ATA
     AGT TGT AAA AGC CAA ACA TAA TGA AGA ATA AGT TTA CAT TAT 760             770             780             790
                 .               .               .               .
     AAA GTA TCA ACA AAA AAT TGT TAA TAT ACC TCT ATA CTT TAA
     TTT CAT AGT TGT TTT TTA ACA ATT ATA TGG AGA TAT GAA ATT 800             810             820    GAL 1   830             840
      .               .               .               .               .
     CGT CAA GGA GAA AAA ACT ATA ATG ACT AAA TCT CAT TCA GAA
     GCA GTT CCT CTT TTT TGA TAT TAC TGA TTT AGA GTA AGT CTT 850             860             870             880
                 .               .               .               .
     GAA GTG ATT GTA CCT GAG TTC AAT TCT AGC GCA AAG GAA TTA
     CTT CAC TAA CAT GGA CTC AAG TTA AGA TCG CGT TTC CTT AAT 890             900             910
                 .               .               .
     CCA AGA CCA TTG GCC GAA AAG TGC GGA ATTC
     GGT TCT GGT AAC CGG CTT TTC ACG CCT TAAG
```

The resulting hybrid promoter has been utilized to express human IFN-γ in yeast. In contrast to the native GPD portable promoter, the hybrid promoter, generally designated GPD(G), is regulated by carbon source. In non-fermentable carbon sources such as lactate, a low basal level of expression is observed. IFN-γ expression is induced 50 to 2000-fold by growth in galactose or lactate plus galactose. Expression levels in glucose are comparable to those in lactate. On the other hand, the presence of glucose along with galactose represses the induction ordinarily observed in the presence of galactose. The native promoter directs comparable levels of IFN-γ expression on either glucose or galactose. These results demonstrate that DNA sequences within $UAS_G$ mediate glucose repression.

The hybrid promoter is capable of regulating transcription independently of the orientation of $UAS_G$ or the presence of multiple inserts of $UAS_G$.

Specifically, a unique SalI site was engineered at a pre-existing AvaII site 240 base pairs 5' to the TATA box homology of the GPD promoter (337 base pairs 5' to the transcription initiation region) to generate pGPD(S)-2. A chemically synthesized gene encoding IFN-γ and which incorporated the yeast PGK untranslated leader and optimal yeast codons was cloned into the unique BamHI site of pGPD(S)-2 to generate pGPD(S)γ4. A subcloned $UAS_G$ fragment was cloned into the SalI site of pGPD(S)γ4 to generate the pGPD(G)γ4 series of plasmids.

These and other aspects of the present invention are illustrated in the following examples.

In Example 1, construction of plasmids useful in practicing the present invention is detailed. In Example 2, construction of IFN-γ expression vectors and the $UAS_G$ regulation thereof is detailed. Example 3 illustrates the plasmid copy numbers in yeast of native and hybrid GPD promoters according to the present invention. Finally, Example 4 illustrates expression of exogenous genes as controlled by the hybrid promoter according to the present invention.

EXAMPLE 1

Plasmids pGPD-2 and pPG70 were constructed as described in Bitter, et al., *Gene,* 32: 263–274 (1984). The plasmid pΔ22(GPD) (A.T.C.C. 75043) was constructed by cloning the GPD HindIII-BamHI portable promoter described in Bitter, et al., supra, into pΔ22, a pBR322 derivative in which the EcoRI site was ligated to the ClaI site according to the procedure as set forth in Bitter, et al., supra.

Plasmid p2-2 contains the 2 kilobase EcoRI fragment of *S. cerevisiae* DNA which includes portions of the coding regions and the 676 base pair intergenic region of the divergently transcribed GAL 1 and GAL 10 genes. Plasmid p2-2 was cloned from an *S. cerevisiae* genome library using the cloned *S. carlsbergensis* GAL 1, GAL 10 gene cluster, as described in Citron, et al., *J.Bacteriol.,* 158: 269–278 (1984), as a hybridization probe.

All recombinant DNA manipulations employ the standard methodologies as described in Maniatis, et al., "Molecular Cloning: A Laboratory Manual", Cold Spring Harbor Laboratories, Cold Spring Harbor, N.Y. (1982), which is incorporated by reference herein.

Figure 1:
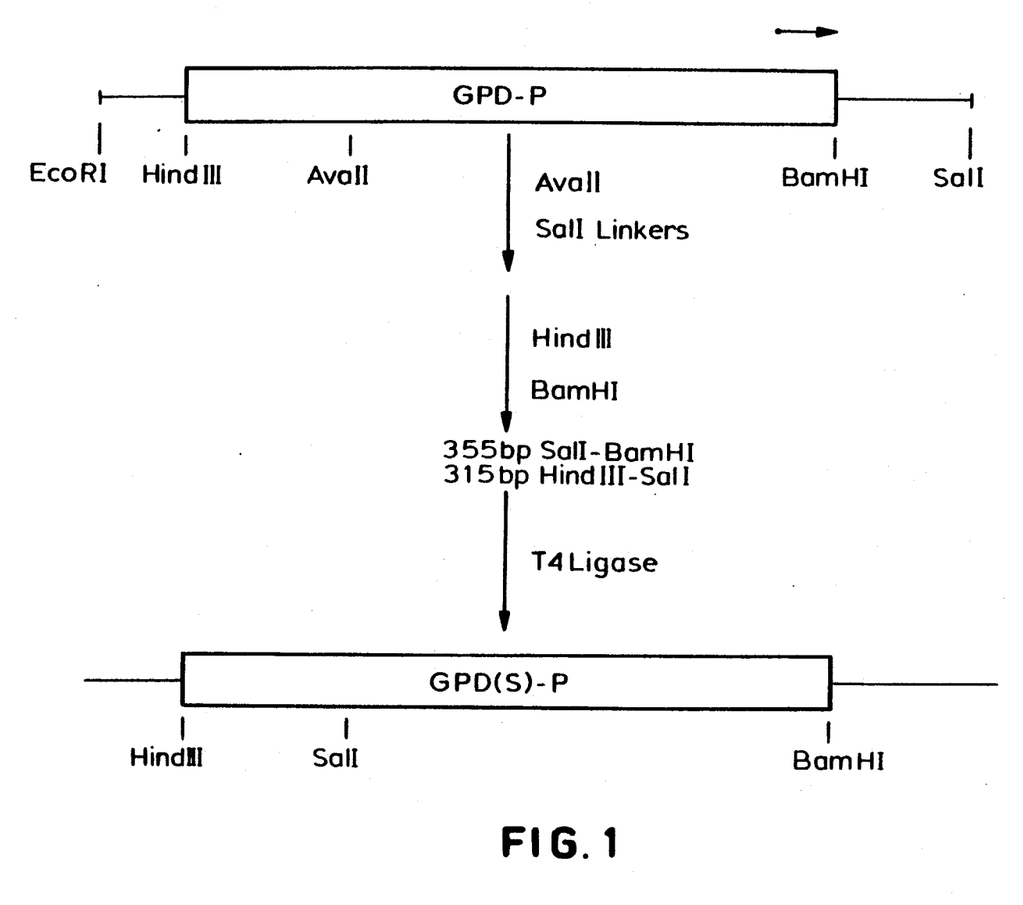
FIG. 1 schematically illustrates the restriction map of a GPD portable promoter and also illustrates the construction of a SalI site within this promoter to obtain the portable promoter GPD(S)

As illustrated in FIG. 1, a unique SalI restriction site was introduced 240 base pairs 5' to the TATA box of the GPD portable promoter. The plasmid pΔ22 (GPD) was digested with EcoRI and SalI and the 950 base pair fragment containing the GPD promoter was purified by agarose gel electrophoresis. This fragment was digested with AvaII which cleaves at position -382 of the GPD promoter, as indicated in Bitter, et al., supra. Cohesive termini were rendered blunt by end-filling with Klenow fragment and SalI linkers, as available from Collaborative Research, Inc., Waltham, Mass., ligated to the fragments. After complete digestion with SalI, the mixture of DNA fragments was restricted with HindIII and BamHI. The resulting 355 base pair and 315. base pair DNA fragments were purified by polyacrylamide gel electrophoresis.

Figure 2:
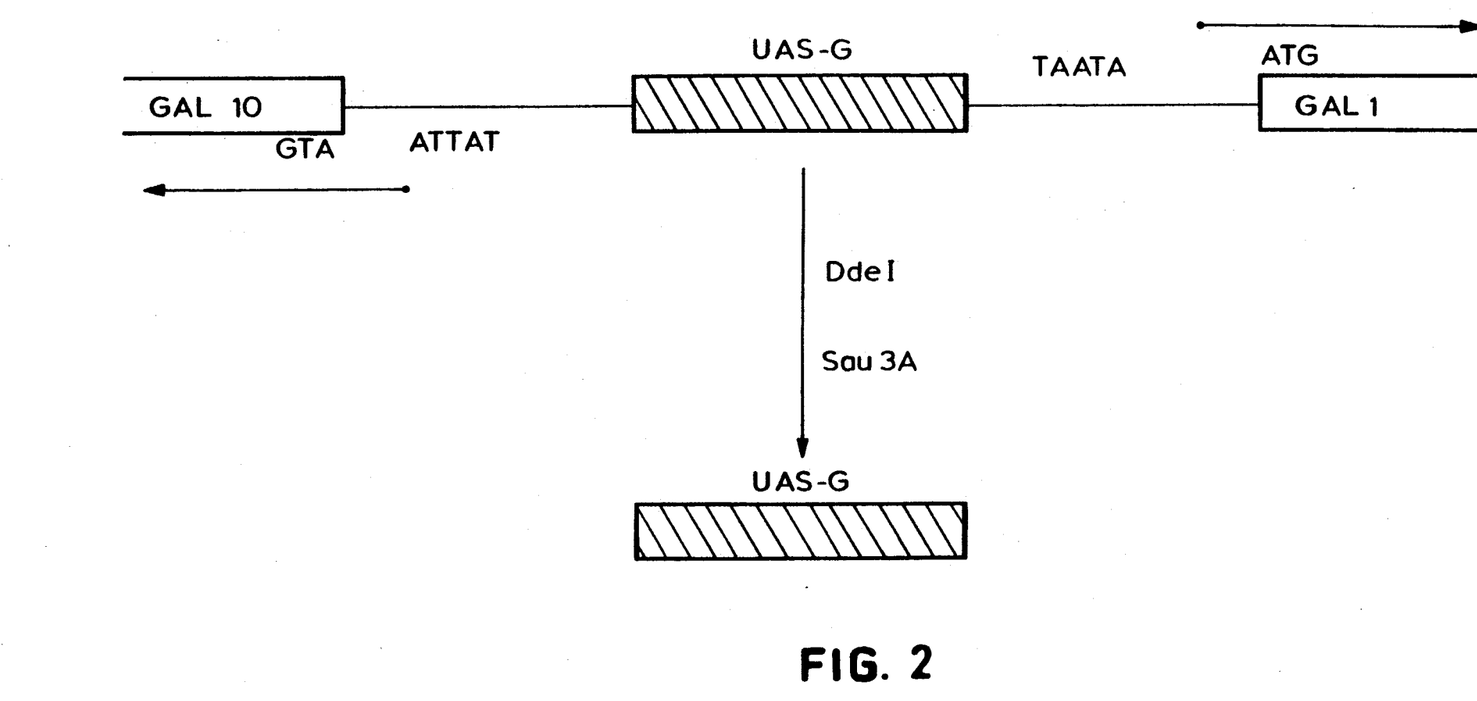
FIG. 2 schematically illustrates the isolation of UAS$_G$ from the plasmid p2-2.

As shown in FIG. 2, the plasmid p2-2 was digested with EcoRI. The resulting 2 kilobase yeast DNA fragment was purified by agarose gel electrophoresis. Digestion of the 2 kilobase fragment with DdeI and SauIIIA yielded a series of smaller fragments including an approximately 365 base pair fragment which was expected to include the $UAS_G$ as described in Guarente, et al., *Proc.Natl Acad.Sci. (U.S.A.),* 79: 7410–7414 (1982). The presence of $UAS_G$ in this fragment was confirmed in Southern blot hybridizations, by demonstrating that only this fragment hybridized with the synthetic oligonucleotide 5'-CAT CGC TTC GCT GAT-3' derived from the sequence for $UAS_G$ as given in Johnston, et al., *Mol.Cell.Biol.,* 4: 1440–1448 (1984). The 365 base pair fragment was purified by agarose gel electrophoresis. SalI linkers were added (as described in Maniatis, et al., supra), and the fragment was cloned into pBR322 to generate pBR($UAS_G$), which was used as a source of $UAS_G$.

Figure 3:
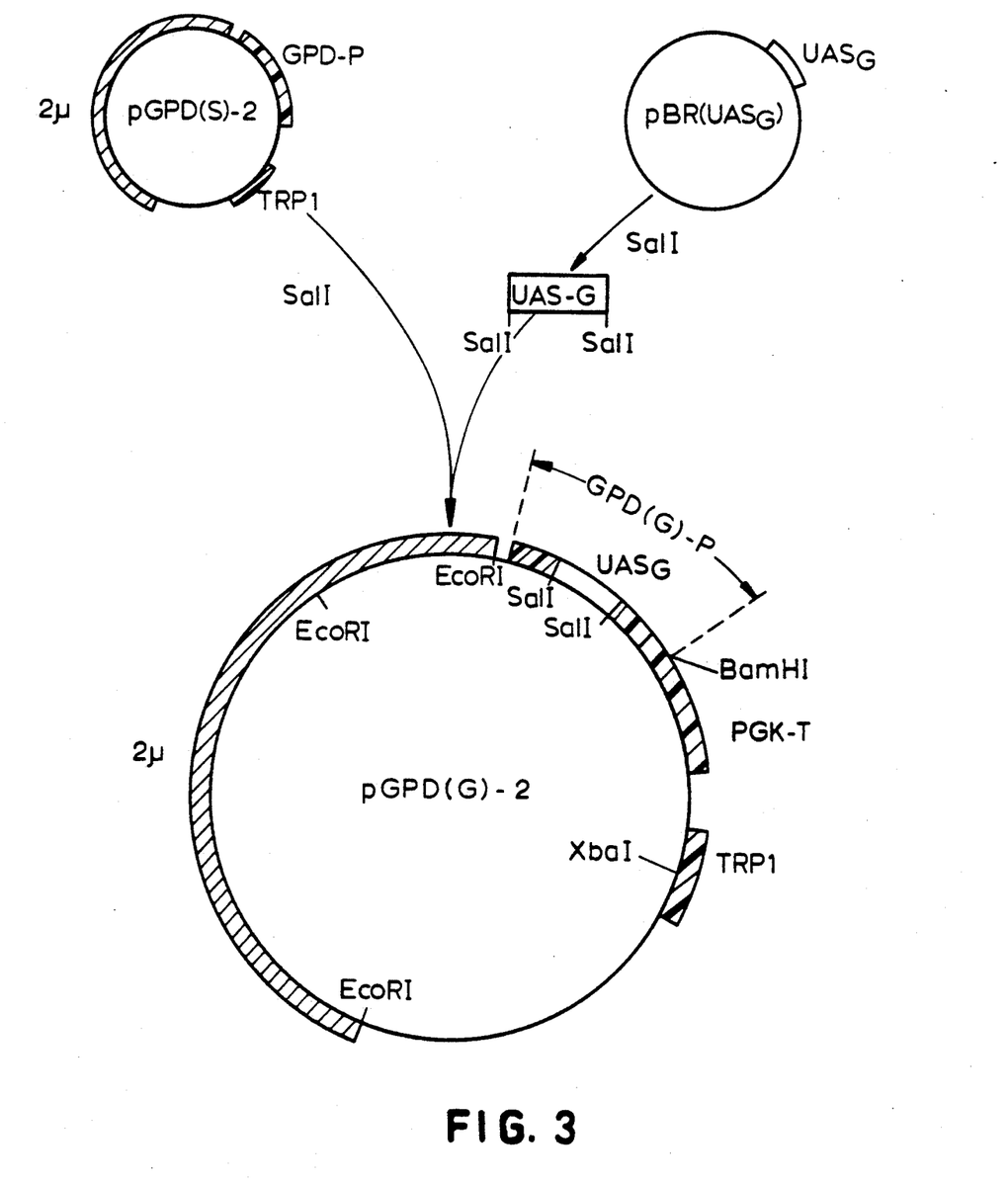
FIG. 3 schematically illustrates techniques used in construction of the plasmid pGPD(G)-2.

The GPD(S) portable promoter, containing a SalI site at position -382, was assembled by cloning the 355 base pair and 315 base pair fragments into HindIII and BamHI cleaved pBR322. The GPD(S) promoter was excised with HindIII and BamHI, and then cloned into pPG70 as described in Bitter, et al., supra, for pGPD-2 in order to generate pGPD(G)-2 as shown in FIG. 3. The pGPD(G)-2 plasmid was deposited with the American Type Culture Collection, Rockville, Md., on Sep. 5, 1991 and assigned A.T.C.C. Accession No. 75094.

EXAMPLE 2

A gene encoding an interferon-γ analog. IFN-γ4A, having the sequence as set forth in Table II, was chemically synthesized using phosphoramidite chemistry according to the procedure of Caruthers, in *Chemical and Enzymatic Synthesis of Gene Fragment,* Verlag Chemie, Weinheim, Federal Republic of Germany, pages 71–79 (1982).

TABLE II

|   | Met | Gln | Asp | Pro | Tyr | Val | Lys | Glu | Ala |
|---|---|---|---|---|---|---|---|---|---|
| AACAACAAATATAAAACA | ATG | CAA | GAT | CCA | TAC | GTT | AAG | GAA | GCT |
| TTGTTGTTTATATTTTGT | TAC | GTT | CTA | GGT | ATG | CAA | TTC | CTT | CGA |

| Glu | Asn | Leu | Lys | Lys | Tyr | Phe | Asn | Ala | Gly | His | Ser | Asp | Val |
|---|---|---|---|---|---|---|---|---|---|---|---|---|---|
| GAA | AAC | TTG | AAG | AAG | TAC | TTC | AAC | GCT | GGT | CAC | TCT | GAC | GTT |
| CTT | TTG | AAC | TTC | TTC | ATG | AAG | TTG | CGA | CCA | GTG | AGA | CTG | CAA |

TABLE II-continued

| Ala | Asp | Asn | Gly | Thr | Leu | Phe | Leu | Gly | Ile | Leu | Lys | Asn | Trp |
|---|---|---|---|---|---|---|---|---|---|---|---|---|---|
| GCT | GAC | AAC | GGT | ACC | TTG | TTC | TTG | GGT | ATC | TTG | AAG | AAC | TGG |
| CGA | CTG | TTG | CCA | TGG | AAC | AAG | AAC | CCA | TAG | AAC | TTC | TTG | ACC |

| Lys | Glu | Glu | Ser | Asp | Arg | Lys | Ile | Met | Gln | Ser | Gln | Ile | Val |
|---|---|---|---|---|---|---|---|---|---|---|---|---|---|
| AAG | GAA | GAA | TCC | GAC | AGA | AAG | ATC | ATG | CAA | TCT | CAA | ATT | GTT |
| TTC | CTT | CTT | AGG | CTG | TCT | TTC | TAG | TAC | GTT | AGA | GTT | TAA | CAA |

| Ser | Phe | Tyr | Phe | Lys | Leu | Phe | Lys | Asn | Phe | Lys | Asp | Asp | Gln |
|---|---|---|---|---|---|---|---|---|---|---|---|---|---|
| TCC | TTC | TAC | TTC | AAG | TTG | TTC | AAG | AAC | TTC | AAG | GAC | GAT | CAA |
| AGG | AAG | ATG | AAG | TTC | AAC | AAG | TTC | TTG | AAG | TTC | CTG | CTA | GTT |

| Ser | Ile | Gln | Lys | Ser | Val | Glu | Thr | Ile | Lys | Glu | Asp | Met | Asn |
|---|---|---|---|---|---|---|---|---|---|---|---|---|---|
| TCT | ATC | CAA | AAG | TCC | GTC | GAA | ACC | ATC | AAG | GAA | GAC | ATG | AAC |
| AGA | TAG | GTT | TTC | AGG | CAG | CTT | TGG | TAG | TTC | CTT | CTG | TAC | TTG |

| Val | Lys | Phe | Phe | Asn | Ser | Asn | Lys | Lys | Lys | Arg | Asp | Asp | Phe |
|---|---|---|---|---|---|---|---|---|---|---|---|---|---|
| GTT | AAG | TTC | TTC | AAC | TCT | AAC | AAG | AAG | AAG | AGA | GAC | GAC | TTC |
| CAA | TTC | AAG | AAG | TTG | AGA | TTG | TTC | TTC | TTC | TCT | CTG | CTG | AAG |

| Glu | Lys | Leu | Thr | Asn | Tyr | Ser | Val | Thr | Asp | Leu | Asn | Val | Gln |
|---|---|---|---|---|---|---|---|---|---|---|---|---|---|
| GAA | AAG | TTG | ACT | AAC | TAC | TCC | GTT | ACC | GAT | TTG | AAC | GTC | CAA |
| CTT | TTC | AAC | TGA | TTG | ATG | AGG | CAA | TGG | CTA | AAC | TTG | CAG | GTT |

| Arg | Lys | Ala | Ile | His | Glu | Leu | Ile | Gln | Val | Met | Ala | Glu | Leu |
|---|---|---|---|---|---|---|---|---|---|---|---|---|---|
| AGA | AAG | GCC | ATT | CAC | GAA | TTG | ATC | CAA | GTT | ATG | GCT | GAA | TTG |
| TCT | TTC | CGG | TAA | GTG | CTT | AAC | TAG | GTT | CAA | TAC | CGA | CTT | AAC |

| Ser | Pro | Ala | Ala | Lys | Thr | Gly | Lys | Arg | Lys | Arg | Ser | Gln | Met |
|---|---|---|---|---|---|---|---|---|---|---|---|---|---|
| TCT | CCA | GCT | GCC | AAG | ACT | GGT | AAG | AGA | AAG | AGA | TCT | CAA | ATG |
| AGA | GGT | CGA | CGG | TTC | TGA | CCA | TTC | TCT | TTC | TCT | AGA | GTT | TAC |

| Leu | Phe | Arg | Gly | Arg | Arg | Ala | Ser | Gln | | | |
|---|---|---|---|---|---|---|---|---|---|---|---|
| TTG | TTC | AGA | GGT | AGA | AGA | GCT | TCC | CAA | TGA | TGAAGTCG | |
| AAC | AAG | TCT | CCA | TCT | TCT | CGA | AGG | GTT | ACT | ACTTCAGC | |

The IFN-γ4A gene includes an untranslated leader region corresponding to the 18 base pairs immediately 5' to the translation initiation codon (ATG) of the native yeast PGK gene. Hitzeman, et al., *Nucleic Acids Res.*, 10: 791-7808 (1982). The coding region employs codons which are preferentially utilized in highly-expressed yeast genes and has a codon bias index of 0.99 when calculated according to the technique of Bennetzen, et al., *J.Biol.Chem.*, 257: 3018-3025 (1982). The sequence of the cloned synthetic IFN-γ gene was determined by subcloning in coliphage M13 and determining the DNA sequence by the dideoxy chain termination technique of Sanger, et al., *Proc.Natl.Acad.Sci. (U.S.A.)*, 74: 5463-5467 (1977).

Figure 4:
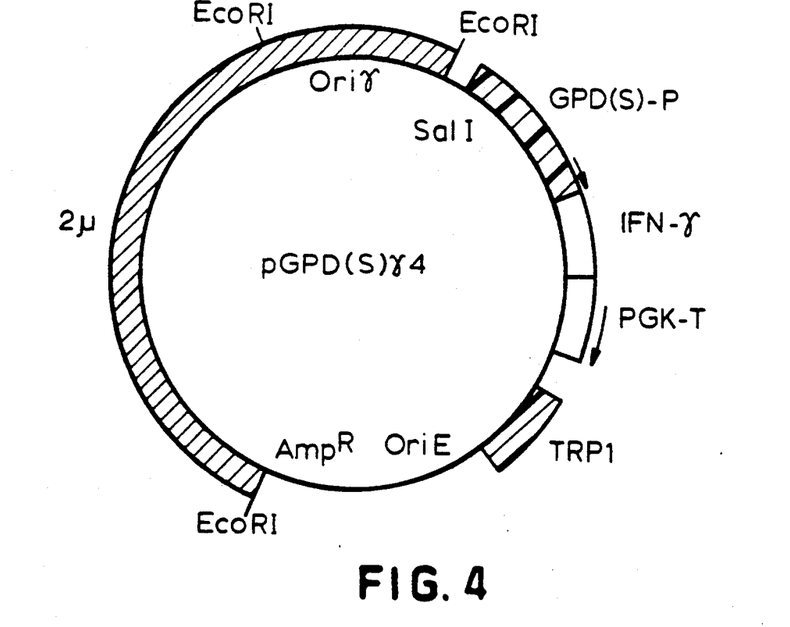
FIG. 4 schematically illustrates the vector GPD(S)γ4.

After confirming the sequence of the cloned synthetic gene, it was excised as a HpaI-SalI fragment, the ends of which were rendered blunt by digestion with mung bean nuclease, available from Miles Laboratories, Elkhart, Ind. Plasmid pGPD(S)-2, prepared as in Example 1, was cleaved with BamHI, cohesive termini were removed as described in Example 1, and the IFN-γ4A gene was cloned in the correct orientation by blunt-end ligation to generate pGPD(S)γ4, as illustrated in FIG. 4.

Figure 5:
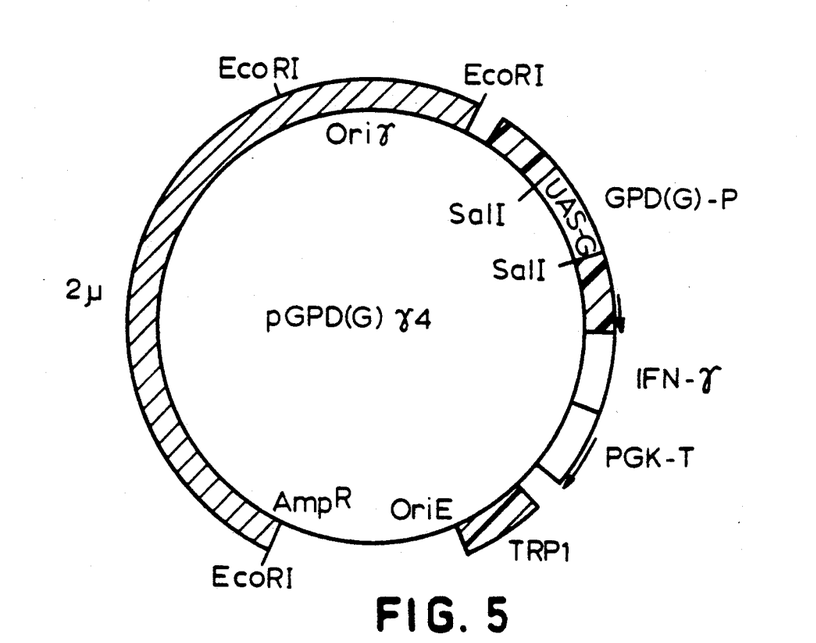
FIG. 5 schematically illustrates the generic vector pGPD(G)γ4.
Figure 6:
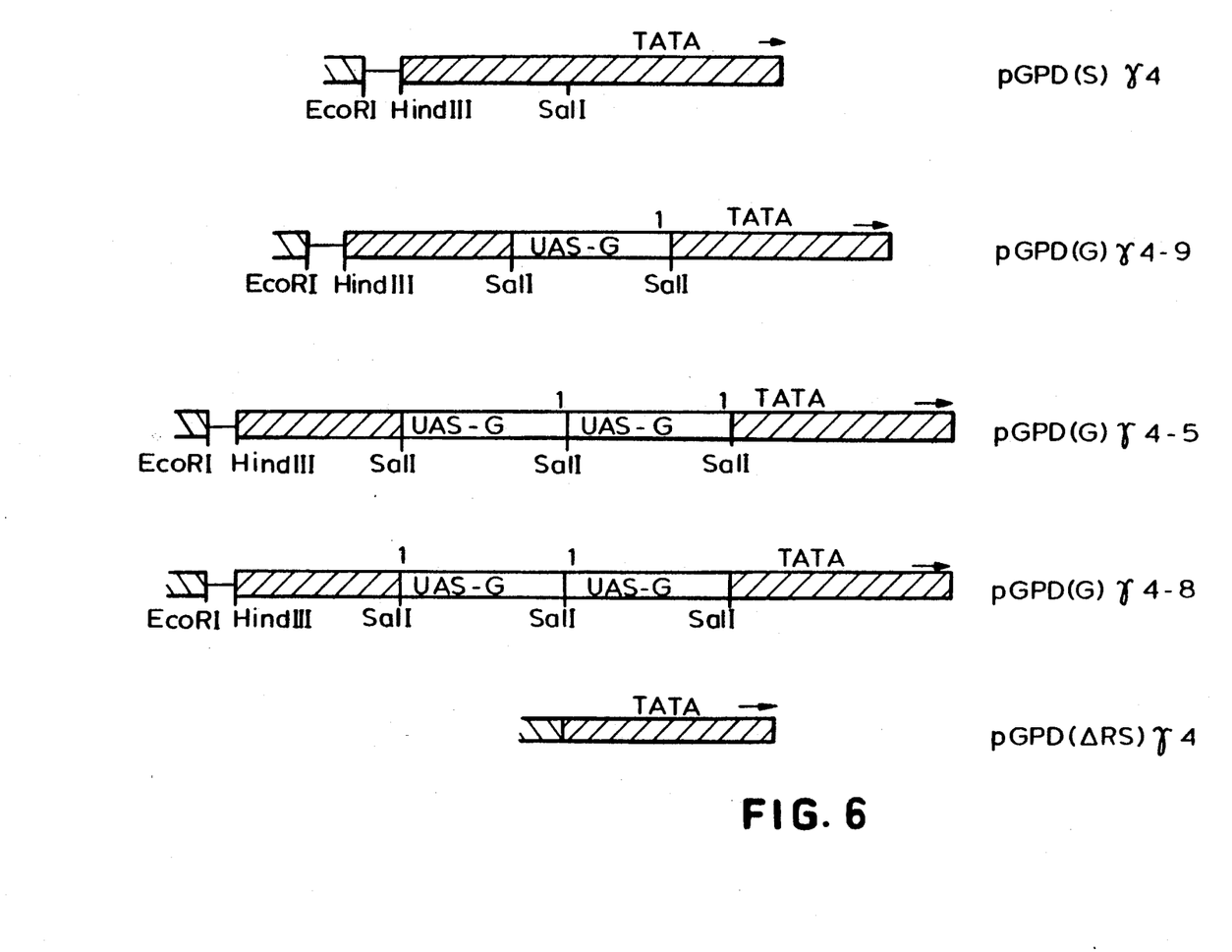
FIG. 6 illustrates variations of the promoter structure in expression vectors according to the present invention.

The vector pGPD(S)γ4 was cleaved with SalI. The plasmid pBR(UAS$_G$) was digested with SalI, a 375 base pair fragment was purified and the fragment cloned into SalI cleaved pGPD(S)γ4 in order to generate the generic pGPD(G)γ4 vector as shown in FIG. 5. The orientation of UAS$_G$ in specific vectors is depicted in FIG. 6. The vector pGPD(G)γ4-9 is the basic orientation of pGPD(G)γ4 illustrated in FIG. 6, wherein the GAL 1 proximal end of UAS$_G$ is denoted by a "I". In the plasmid pGPD(G)γ4-5, two copies of the UAS$_G$ insert were determined by means of the restriction enzyme mapping to be inserted head to tail. The vector pGPD(G)γ4-8 also has two copies of the UAS$_G$ sequence, but these are inverted relative to the copies found in the sequence of pGPD(G)γ4-5.

Complete digestion of pGPD(S)γ4 with SalI was followed by partial EcoRI digestion, end-filling with Klenow fragment available from Collaborative Research, Inc., Waltham, Mass., and religation in order to generate the vector pGPD(ΔRS)γ4, in which the DNA from the EcoRI site at the 2μ/pBR322 border to the SalI site of the GPD promoter, a total of 344 base pairs, was deleted.

J17-3a host cells for use according to the present invention were *S. cerevisiae* cells derived from the J17 strain [Fitzgerald-Hayes, et al., *Cell*, 29: 235-244 (1982)], which was cured of the endogenous 2μ plasmid as described in Tschumper, et al., *Gene*, 23: 221-232 (1983). Alternatively, a strain designated DM-1 (MATa/MATα, trpl, cir°) [ATCC No. 20749, deposited Apr. 5, 1985] was constructed by mating strain RH218 [Miozarri, et al., *J.Bacteriol.*, 134: 48-54 (1978)] (a, gal 2, TRP1, cir°), and strain J17-3A (α, ade 1, his 2, met 14, ura 3, trpl, cir°). Vectors were introduced into the host cells by either the spheroplast method according to Hinnen, et al., *Proc.Natl.Acad.Sci. (U.S.A.)*, 75: 1929-1933 (1978).

Transformants were selected in 0.67% yeast nitrogen base without amino acids (YNB) and 2% glucose containing 0.5% casamino acids. Transformants were cultured in 0.67% YNB, 0.5% casamino acids, and the carbon sources appropriate to the experiment performed. All strains were maintained in media containing glucose as the carbon source.

IFN-γ was quantitated in whole cell extracts by an end-point cytopathic effect assayed according to Weck, et al., *J.General Virology*, 57: 233-237 (1982). From a log phase culture, 10 OD-ml (equivalent number of cells to 10 ml of an OD-1 culture) were removed and the cells collected by centrifugation. After washing with water, the cell pellet was re-suspended in 0.2 ml 50 mM tris-HCl at pH 8.0; 6M urea; and 1 mM phenylmethyl sulfonyl fluoride (PMSF), and lysed by vortexing with glass beads. Dilutions of the whole cell extract were made in Dulbecco's Minimal Essential Medium with 2% fetal calf serum.

Promoter activity of the various constructs was initially monitored by bioassay measurement of IFN-$\gamma$ production. Such a bioassay accurately quantitates IFN-$\gamma$ at very low expression levels and thus was used to measure relative promoter activity under various metabolic conditions. Because the transcript initiation and termination sites of the different vectors appear to be identical, it is unlikely that differential translation efficiencies of the IFN-$\gamma$ mRNA occur in different strains or under different growth conditions. Therefore, IFN-$\gamma$ expression determined by bioassay may be used as an indirect measurement of promoter activity.

Starter cultures of strain DM-1 harboring either pGPD(S)$\gamma$4 or pGPD(G)$\gamma$4-9 were grown to saturation in the media described above containing 2% glucose, were inoculated into selected media containing the sugars indicated in Table IV at 2%, and cultured overnight. Host cell extracts were prepared by glass bead lysis and IFN-$\gamma$ was quantitated by an end-point cytopathic effect assay.

TABLE III

| Strain | Expression Vector | Units IFN-$\gamma$/OD-1 | | | | |
|---|---|---|---|---|---|---|
| | | Glucose | Galactose | Galactose Glucose | Lactate | Galactose Lactate |
| DM-1 | pGPD(S)$\gamma$4 | $1.6 \times 10^7$ | $1.3 \times 10^7$ | $1.3 \times 10^7$ | — | $8 \times 10^6$ |
| DM-1 | pGPD($\Delta$RS)$\gamma$4 | $8.3 \times 10^5$ | $8.3 \times 10^5$ | — | — | — |
| DM-1 | pGPD(G)$\gamma$4-9 | $3.3 \times 10^5$ | $3.9 \times 10^7$ | $7.0 \times 10^6$ | $9.2 \times 10^6$ | $2.1 \times 10^7$ |
| J17-3a | pGPD(G)$\gamma$4-8 | $1.9 \times 10^5$ | $3.9 \times 10^7$ | $7.2 \times 10^6$ | $9.4 \times 10^4$ | $2.4 \times 10^7$ |

The native GPD(S) promoter produced approximately $1.6 \times 10^7$ units of IFN-$\gamma$ per OD-L (i.e., normalized to one liter of culture at an optical density of 1) culture. Assuming a specific activity of $1 \times 10^7$ units per milligram of protein for IFN-$\gamma$, this expression level corresponds to 1–2% of the total cell protein.

In general, the expression level from pGPD(S)$\gamma$4 in glucose is equivalent or slightly higher than that obtained when the cells are grown in galactose, lactate or galactose plus lactate. It has been reported that glyceraldehyde-3-phosphate dehydrogenase enzyme activity is induced 1,000-fold by growth on glucose. Maitra, et al., *J.Biol.Chem.*, 246: 475 (1971). The results, shown in Table III, suggest that such increased GPD activity must be due in large part to an increase translational efficiency of pre-existing GPD mRNA, or increased enzyme activity or stability. Alternatively, the 651 base pair GPD promoter segment utilized in this example, may not contain all DNA sequences necessary for full glucose induction of transcription.

The hybrid GPD(G) promoter exhibits a strikingly different regulation of expression by carbon source. As shown in Table III, the IFN-$\gamma$ expression level is markedly reduced by growth in glucose, compared to the native promoter, and the hybrid promoter is induced 100- to 200-fold by growth in galactose. Expression of the hybrid promoter in lactate is variable but always less than observed with galactose as the carbon source. Full induction is observed by growth in lactate plus galactose. By contrast, only a 20- to 40-fold induction is observed by growth in 2% glucose plus 2% galactose.

These results demonstrate several functional states of the hybrid promoter. The promoter is induced by the presence of galactose. It is uninduced in lactate and repressed in glucose. The degree of glucose repression observed in this experiment (glucose+galactose) may be an underestimate because the glucose concentration was depleted during growth of the culture (see discussion of FIG. 8 below).

Figure 7:
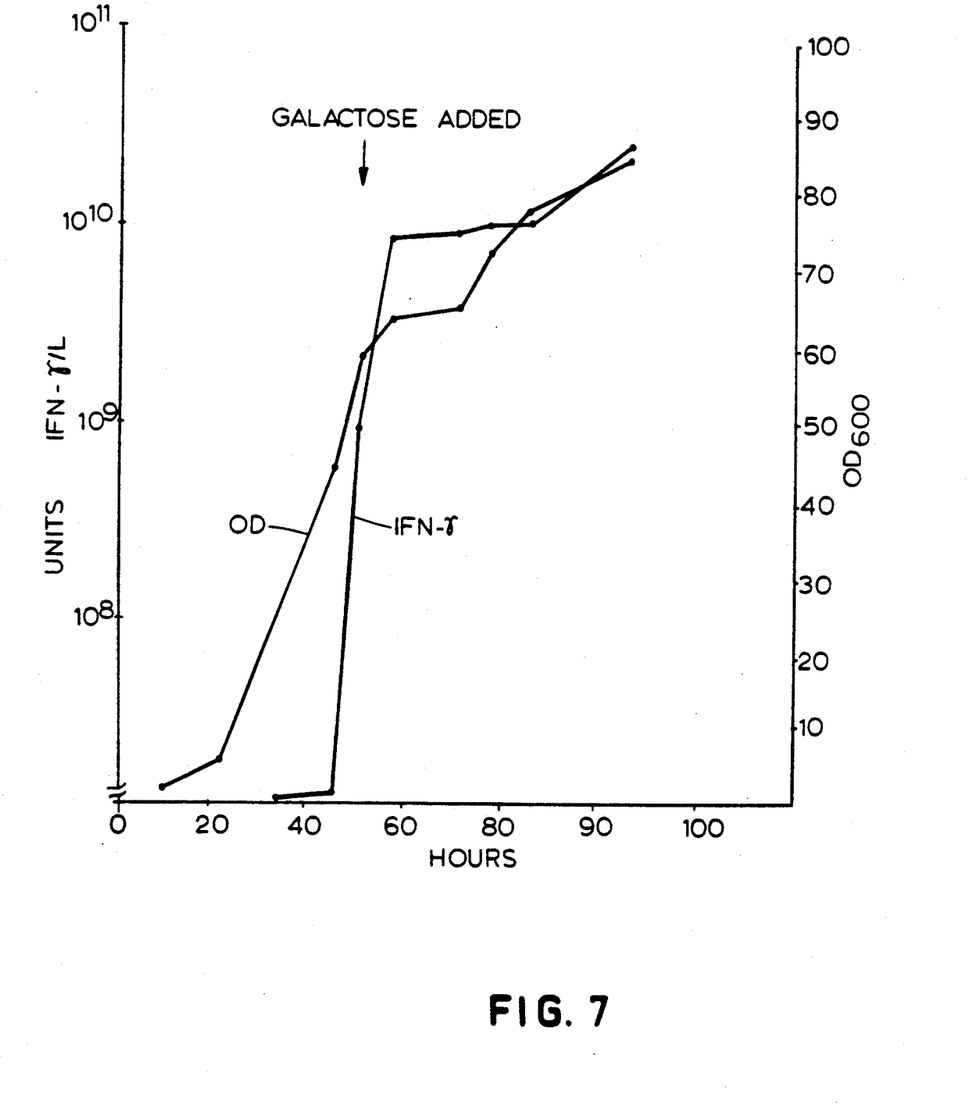
FIG. 7 is a graph illustrating galactose induction of IFN-γ expression in a culture of yeast cells pGPD(G)γ4-9.

In an illustration of IFN-$\gamma$ production using the hybrid promoter according to the present invention, host cells of strain DM-1 containing the vector pGPD(G)$\gamma$4-8 were inoculated into a 16-liter fermentor containing 10 liters of selective medium, as indicated above. The cells were cultured at 30° C. with aeration and a limited glucose feed. Galactose was added to 10 g/l at 48 hours and periodically thereafter. Cells were sampled at various times and IFN-$\gamma$ in whole cell extracts determined by bioassay as above. These culture conditions resulted in a 2,000-fold induction and a final yield of $2.2 \times 10^{10}$ units of IFN-$\gamma$ per liter of culture, as indicated in FIG. 7.

Figure 8:
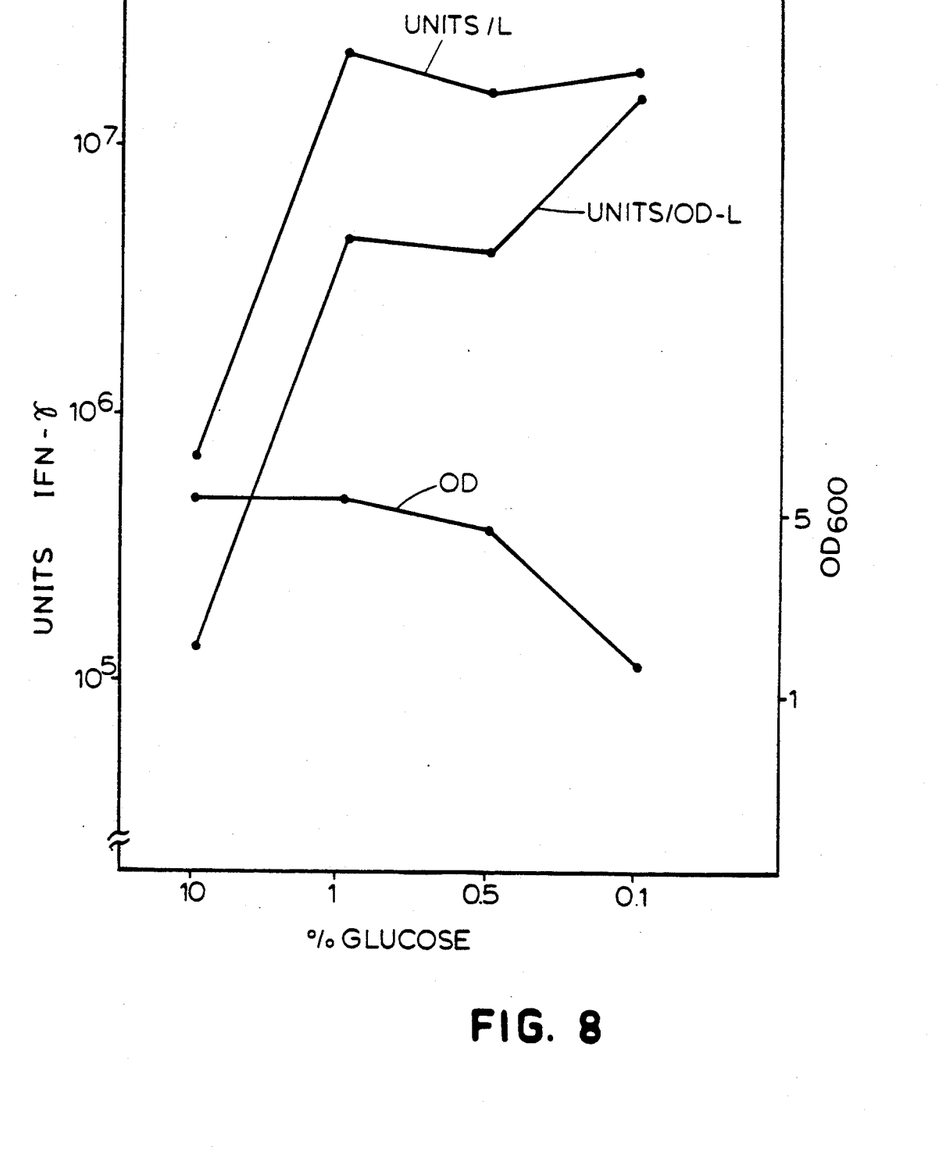
FIG. 8 illustrates glucose repression of the GPD(G)γ4-9 promoter according to the present invention.

In another experiment, *S. cerevisiae* DM-1 cells harboring pGPD(G)$\gamma$4-9 was cultured to saturation in selective media containing 2% glucose. The culture was diluted 1:1000 in selective media containing 2% galactose and the glucose concentrations as indicated in FIG. 8. The cells were cultured overnight to yield the cell densities (OD) as further indicated in FIG. 8. IFN-$\gamma$ in whole cell extracts was quantified by an end-point cytopathic inhibition assay as above and the results were plotted as Units/L culture or as Units/OD-L culture.

The results graphically depicted in FIG. 8 further demonstrate repression of the promoter by glucose. It is also apparent from FIG. 8 that galactose induction may be obtained even when glucose is present in the medium. A practical consequence of this result is that cells may be cultured in media containing glucose to obtain repression of the expression of an exogenous gene and that induction of expression of the exogenous gene may be obtained by adding galactose to the medium, providing the glucose concentration is maintained below the basal level required for repression.

EXAMPLE 3

To examine the plasmid copy number of the vectors containing various promoters according to the present invention, a DNA fragment including the 3' coding region of the yeast PGK gene was used as a hybridization probe. Because the expression vectors employ this same DNA fragment as a transcription termination signal, this probe allows detection of both the native chromosomal PGK gene and the plasmid-borne fragment containing the PGK terminator, which may be separated by size in a Southern Blot format. In these experiments, the chromosomal PGK gene was used as an internal control for quantitating plasmid copy number.

A hybridization probe for the Southern Blot technique was prepared by nick translation (Maniatis, et al., supra) of the PGK terminator, the BglII-HindIII 380 base pair fragment described in Hitzeman, et al., *Nucleic Acids Res.*, 10: 7791-7808 (1982). Blots were pre-hybridized in 5×SSPE, 5×Denhardt's solution, 0.5% SDS, and 100 μg/ml of denatured salmon sperm DNA for 60 minutes at 60° C. Hybridizations were performed in 5×SSPE, 1×Denhardt's solution, 0.5% SDS, 100 μg/ml of denatured salmon sperm DNA, and greater than $10^6$ cpm of probe having a specific activity of greater than $10^7$ cpm/μg of DNA.

Host cell DNA was extracted from log phase yeast cultures converted to spheroplasts in 1.0M sorbitol, 0.1M sodium citrate, 0.06M $Na_2EDTA$ (pH 5.8), and 2% β-mercaptoethanol by incubation with 4 mg/ml of Zymolyase (Miles Laboratories, Elkhart, Ind.) at 37° C. for 10-20 minutes. The spheroplasts were collected by centrifugation and lysed by re-suspension in 20 mM tris-HCl (pH 7.5), 50 mM $NH_4Cl$, 10 mM KCl, 6 mM $MgCl_2$, and 0.1% Triton X-100. SDS and proteinase K (Miles Laboratories, Elkhart, Ind.) were added to 0.5% and 50 μg/ml, respectively, and the extract was incubated at 37° C. overnight. The suspension was extracted several times with phenol:chloroform (1:1), followed by precipitations in 50% isopropanol and then in 70% ethanol.

The DNA was digested with the restriction enzyme appropriate to the experiment, fractionated by size in a 0.7% agarose gel in a TBE buffer according to Maniatis, et al., supra, and transferred to a BA 85 nitrocellulose filter (available from Schleicher & Schuell, as described in Thomas, *Proc.Natl.Acad.Sci. (U.S.A.)*, 77: 5201-5205 (1980).

The results of the Southern Blot analyses are presented in Table IV.

TABLE IV

| Lane | Transformant | Culture Conditions | Plasmid Copy Number/Cells |
|---|---|---|---|
| 1 | pGPD(S)γ4 | Glucose | approx. 1 |
| 2 | pGPD(G)γ4-9 | Glucose | 60 |
| 3 | pGPD(G)γ4-9 | Galactose (3 generations) | 30-60 |
| 4 | pGPD(G)γ4-9 | Galactose (serially 50 generations) | approx. 1 |

As indicated in Table IV, the strain DM-1 exhibits widely varying plasmid copy numbers when transformed with different vectors. The vector pGPD(S)γ4 is present at less than one copy per cell. In contrast, pGPD(G)γ4-9, in cells maintained in glucose, exhibits a copy number of approximately 60 per cell. DM-1 harboring pGPD(G)γ4-9, which had been maintained in glucose and then grown overnight (4 to 5 generations) in galactose, similarly exhibited a plasmid copy number of 30 to 60 per cell.

The different copy numbers of the native and hybrid promoter vectors may be due to DNA sequence effects on plasmid stability or, alternatively, caused by expression of IFN-γ. This latter possibility was tested by serially culturing strain DM-1 carrying pGPD(G)γ4-9 in galactose for more than 50 generations. The plasmid copy number of this culture dropped to less than one per cell.

This is a direct demonstration that the expression of the IFN-γ gene decreases plasmid stability. Apparently, IFN-γ is toxic to yeast and this toxicity is responsible for the low copy number of pGPD(S)γ4 maintained in glucose.

The results in Table IV also show that even in the case of gene product toxicity, the hybrid promoter according to the present invention may be employed to obtain high plasmid copy number (e.g., 60, as in Table IV) by repressing the promoter with glucose. Consequently, when the promoter is induced with galactose, greater expression of the exogenous gene may be obtained than with the native promoter which is present at low copy number. Thus the present invention solves the problem of exogenous gene product toxicity by providing for a high-density cell culture while permitting high levels of exogenous gene expression on demand.

EXAMPLE 4

Two hepatitis B surface antigen exogenous genes, the gene (HBs) for mature hepatitis B surface antigen (HBsAg), and the gene (PreS) for pre-S hepatitis B surface antigen (Pre-S HBsAG, which contains an additional 174 amino acids coded for by the PreS region of the hepatitis B genome), were respectively cloned into the pGPD(G)-2 and pGPD(G')-2 plasmids as described above in Examples 1 and 2 for IFN-γ.

Both pGPD(G)-2 (A.T.C.C. 75094) and pGPD(G')-2 were derived from pGPD(S)-2 and pBR(UAS$_G$). The plasmid pBR(UAS$_G$) was cleaved with SalI to isolate UAS$_G$, which was purified on an agarose gel. The plasmid pGPD(S)-2 was cleaved with SalI. The cleaved plasmid was mixed with UAS$_G$ and ligated according to standard procedures (Maniatis, et al., supra). The ligation mixture was transformed into *E. coli* and plasmid DNA in individual clones from the mixture and those containing pGPD(G)-2 and pGPD(G')-2 were identified and examined by restriction enzyme analysis. The clone designated pGPD(G)-2 contained a single UAS$_G$ wherein the GAL 1 proximal end was oriented toward the TATA box homology of the GPD portable promoter. The clone designated pGPD(G')-2 contained a single UAS$_G$ in the opposite orientation of that in pGPD(G)-2.

Figure 9:
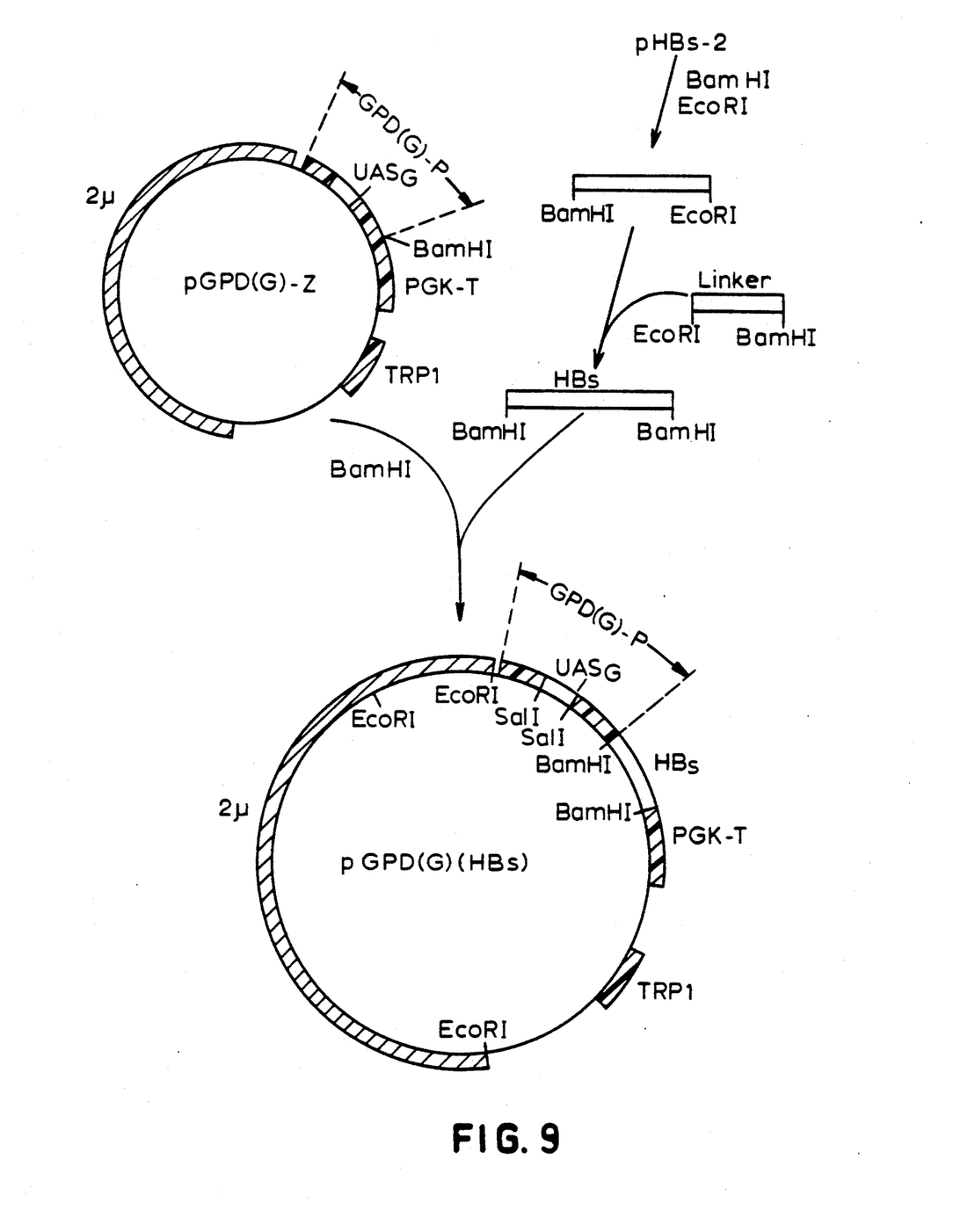
FIG. 9 schematically illustrates techniques used in construction of the vector pGPD(G)(HBs)

As illustrated in FIG. 9, the HBs gene was obtained from the plasmid pHBs-2 (Bitter, et al., supra). The pHBs-2 plasmid was restricted with BamHI and EcoRI under the same general conditions as indicated for Examples 1 and 2, above. An EcoRI-BamHI linker

5'-AAT TCT TGA CTC G
      GA ACT GAG CCT AG-3' was prepared by hybridizing two single-stranded oligonucleotides which were synthesized according to the procedure of Caruthers, supra. Hybridization and ligation of the EcoRI end of the linker with the EcoRI end of the fragment resulting from restriction of pHBs-2 produces a segment of double-stranded DNA with two BamHI ends suitable for insertion into pGPD(G)-2, as described in Example 2, above, in order to obtain the vector pGPD(G)(HBs).

For expression of the PreS gene, the plasmid pSVST-HBV was used. Plasmid pSVST-HBV was constructed from the plasmid pSV4SET (constructed as disclosed in co-owned, co-pending U.S. patent application Ser. No. 584,132, filed Feb. 27, 1984, by Jeffrey K. Browne, entitled "Papova Virus Construction", the disclosure of which is specifically incorporated by reference herein) and from a hepatitis B genome fragment designated HBV. A hepatitis B genome of serotype ADW (Valenzuela, et al., pages 57-70 in *Animal Virus Genetics*, B. Fields, et al., eds., Academic Press, New York) was digested with HhaI and a 1660 base pair fragment was isolated. The HhaI ends were rendered blunt by end-filling and SalI linkers (Collaborative Research, Waltham, Mass.) were added to the HhaI fragment which was cloned into a SalI-cleaved pSV4SET plasmid to obtain the plasmid pSVST-HBV.

Figure 10:
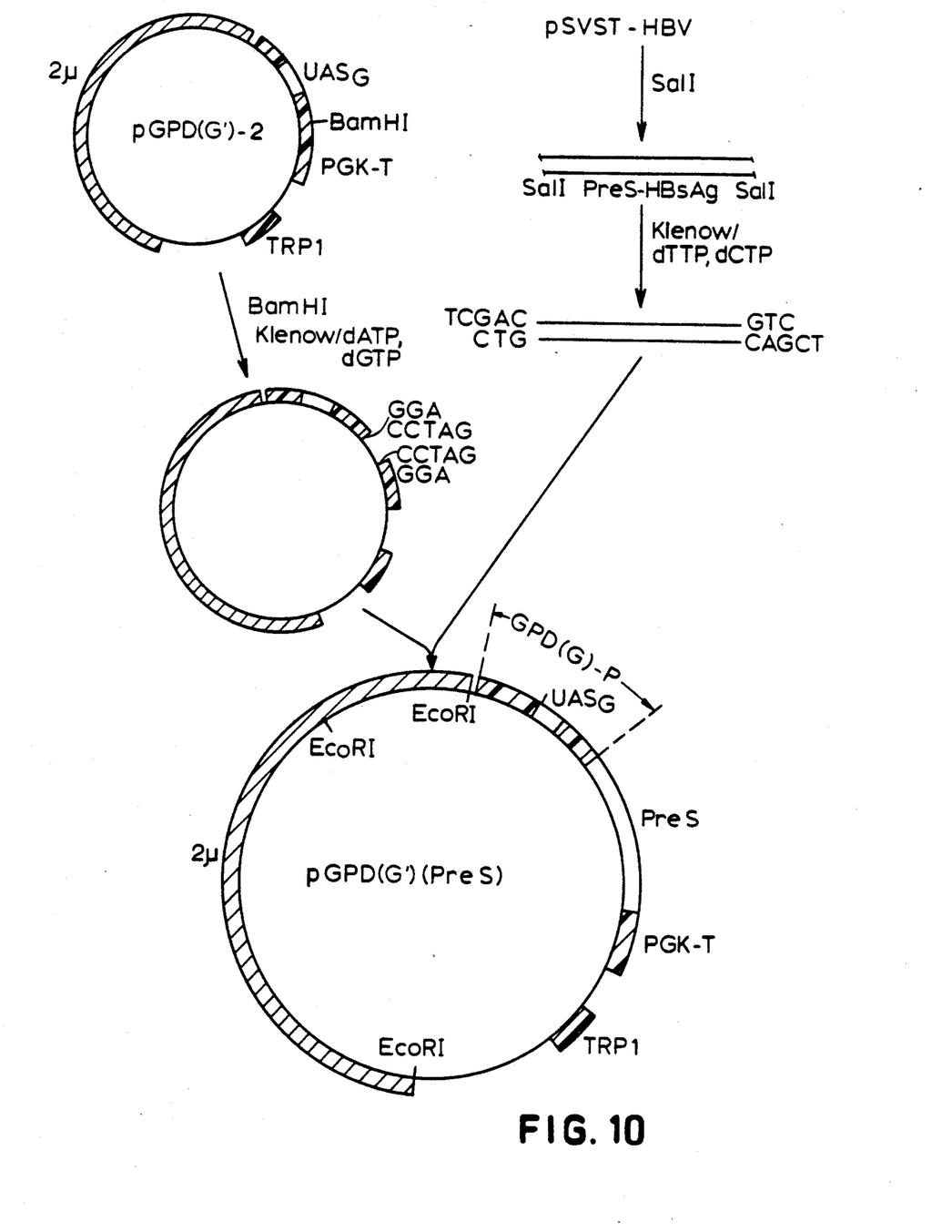
FIG. 10 schematically illustrates techniques used in the construction of the vector pGPD(G)(PreS)

The plasmid pSVST-HBV was restricted in SalI as generally described above, to produce a PreS gene fragment with two SalI ends, as shown in FIG. 10. This DNA fragment was treated with Klenow fragment in the presence of dTTP and dCTP to generate ends which are complementary to BamHI cohesive termini. The plasmid pGPD(G)-2 (A.T.C.C. 75094) was restricted with BamHI. The PreS gene second fragment and the restricted plasmid were then annealed and ligated to produce the plasmid pGPD(G)(PreS).

DM-1 cells were transformed by the pGPD(G)(HBs) and pGPD(G)(PreS) vectors and cultured as described in Example 2, above. Levels of heterologous protein expression as measured by Auszyme II immunoassay (Abbott Laboratories, North Chicago, Ill.) were obtained as shown in Table V.

TABLE V

| Strain | Vector | Product | Expression | |
|---|---|---|---|---|
| | | | Glucose | Galactose |
| DM-1 | pGPD(G)(HBs) | HBsAg | Not detectable | 16 μg/OD-1 |
| DM-1 | pGPD(G)(PreS) | Pre S-HBsAg | Not detectable | 28 μg/OD-1 |

These results demonstrate that the expression of heterologous proteins other than IFN-γ may be regulated by the promoter according to the present invention.

It is expected that numerous modifications and variations will occur to those skilled in the art upon consideration of the present invention. For example, it would be clear to one skilled in the art that the length of the UAS sequence, the length of the promoter sequence, and the position of the UAS sequence within the promoter sequence may be varied. Also, promoters for other isozymes of GPD and UASs other than $UAS_G$ may be employed according to the present invention. Consequently, it is intended that the present invention be given the full scope of the appended claims.

What is claimed is:

1. A hybrid promoter which functions is control transcription of an exogenous gene in yeast comprising:
   a portion of a yeast glyceraldehyde-3-phosphate dehydrogenase promoter effective for promoting transcription;
   a TATA box homology adjacent a downstream end of the hybrid promoter; and
   an insert comprising an extrinsic upstream regulatory sequence at a location in said glyceraldehyde-3-phosphate dehydrogenase promoter upstream of said TATA box homology.

2. The hybrid promoter as recited in claim 1 wherein said upstream activating sequence is an upstream regulatory sequence which is both inducible and repressible.

3. The hybrid promoter as recited in claim 2 wherein said upstream regulatory sequence is inducible by galactose.

4. The hybrid promoter as recited in claim 2 wherein said upstream regulatory sequence is repressible by glucose.

5. The hybrid promoter as recited in claim 1 wherein said upstream regulatory sequence is regulatable by a culture medium carbon source.

6. The hybrid promoter as recited in claim 1 wherein said upstream regulatory sequence comprises an upstream regulatory sequence from a GAL 1-GAL 10 intergenic region.

7. The hybrid promoter as recited in claim 6 wherein said GAL 1-GAL 10 intergenic region is a *Saccharomyces cerevisiae* intergenic region.

8. The hybrid promoter as recited in claim 1 wherein said glyceraldehyde-3-phosphate dehydrogenase promoter is a yeast glyceraldehyde-3-phosphate dehydrogenase promoter.

9. The hybrid promoter as recited in claim 8 wherein said yeast glyceraldehyde-3-phosphate dehydrogenase promoter is a *Saccharomyces cerevisiae* glyceraldehyde-3-phosphate dehydrogenase promoter.

10. A DNA segment mediating regulatable transcription in yeast comprising:
    a hybrid promoter which functions to control transcription of an exogenous gene in yeast comprising:
    a portion of a yeast glyceraldehyde-3-phosphate dehydrogenase promoter effective for promoting transcription;
    a TATA box homology adjacent a downstream end of the hybrid promoter;
    an insert comprising a portion of any extrinsic upstream regulatory sequence at a location in said glyceraldehyde-3-phosphate dehydrogenase promoter upstream of said TATA box homology, said insert functioning to regulate transcription; and
    an exogenous gene downstream of said TATA box homology.

11. The DNA segment mediating regulatable transcription as recited in claim 10 wherein said exogenous gene comprises a DNA sequence encoding a biologically active portion of a γ-interferon.

12. The DNA segment mediating regulatable transcription as recited in claim 11 wherein said γ-interferon is a human γ-interferon.

13. The DNA segment mediating regulatable transcription as recited in claim 10 wherein said exogenous gene is a hepatitis B surface antigen gene.

14. The DNA segment mediating regulatable transcription as recited in claim 13 wherein said hepatitis B surface antigen gene is a pre S-HBsAg gene.

15. The DNA segment mediating regulatable transcription as recited in claim 13 wherein said hepatitis B surface antigen gene is a HBsAg gene.

16. A method for controlling transcription of a gene in yeast comprising the steps of:
    inserting a portion of an extrinsic upstream activating sequence upstream of a TATA box homology in a yeast glyceraldehyde-3-phosphate dehydrogenase promoter, said portion functioning to regulate transcription; and
    introducing an exogenous gene downstream of the TATA box homology.

17. The method as recited in claim 16 further comprising the step of inducing the promoter with galactose.

18. The method as recited in claim 16 further comprising the step of repressing the promoter with glucose.

* * * * *